United States Patent [19]

Tomalia

[11] 3,996,237
[45] Dec. 7, 1976

[54] OXAZOLINE- OR OXAZINE-SUBSTITUTED ACRYLIC ESTERS

[75] Inventor: Donald A. Tomalia, Midland, Mich.

[73] Assignee: The Dow Chemical Company, Midland, Mich.

[22] Filed: July 17, 1974

[21] Appl. No.: 489,302

[52] U.S. Cl. .................. 260/307 F; 260/244 R; 260/246 R; 526/260; 526/312
[51] Int. Cl.² .............. C07D 265/08; C07D 263/12
[58] Field of Search .................. 260/307 F, 244 R

[56] References Cited

UNITED STATES PATENTS 3,476,712  11/1969  Fukui et al. ................... 260/78
3,928,499  12/1975  Tomalia ................... 204/159.160

OTHER PUBLICATIONS

Saegusa, *CHEMTECH*, 295 (1975).
Frump – *Chem. Rev.* 1971, vol. 71, No. 5 – pp. 483, 495.

Primary Examiner—Alton D. Rollins
Assistant Examiner—Mark L. Berch
Attorney, Agent, or Firm—L. Wayne White

[57] ABSTRACT

New esters are described having the formula

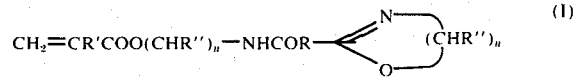

(I)

wherein R is a chemical bond or an inert linking group such as alkylene, oxa-alkylene, thia-alkylene, arylene, alkenylene or the like, R' and R" are H or lower alkyl and n is 2–3. They are made by the reaction of a bis-oxazoline or -oxazine with an equimolar amount of an acrylic acid:

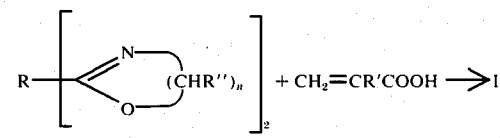

The compounds (I) are acrylic esters and are polymerizable and copolymerizable by the same general techniques used with other acrylic esters, thus producing solid resins useful as molding and coating materials. The oxazoline and oxazine rings in such resins are reactive with carboxyl groups; hence, the resins can be mixed with carboxy-containing polymers to form mixtures that readily cure upon mild heat treatment to form hard, water-resistant and solvent-resistant, infusible resins.

2 Claims, No Drawings

OXAZOLINE- OR OXAZINE-SUBSTITUTED ACRYLIC ESTERS

BACKGROUND OF THE INVENTION

E. M. Fry, J. Org. Chem., 15, 802 (1950) and T. Kagiya et al., Polymer Letters, 4, 257 (1966) have shown that oxazoline rings are opened by carboxylic acids, thus producing the corresponding esters of the acid.

Bis-oxazolines and -oxazines suitable for use in making the compounds of the present invention have been disclosed by Tomalia and Paige in U.S. Pat. No. 3,563,920 and by Tomalia and Sheetz in U.S. Pat. No. 3,763,177.

The use of bis-oxazolines as cross-linking and curing agents for carboxyl-containing polymers has been disclosed by Thill in U.S. Pat. No. 3,758,629.

Fukui et al., U.S. Pat. No. 3,476,712 teach that bis-oxazolines react when heated with dicarboxylic acids to produce polymeric ester-amides.

SUMMARY OF THE INVENTION

Novel acrylic esters are produced by the reaction of a bis-oxazoline or -oxazine with a substantially equimolar amount of an acrylic acid according to the following equation:

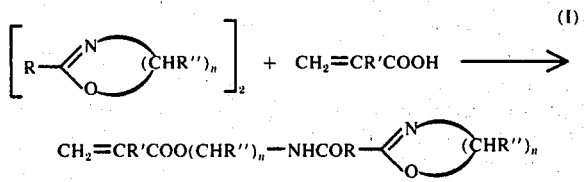

wherein R is a chemical bond or and inert linking group such as alkylene, oxa-alkylene, thia-alkylene, alkenylene or arylene, R and R' are H or lower alkyl and $n$ is 2 or 3. The compounds (I) are acrylic esters and, as such, are homopolymerizable and copolymerizable with other vinyl monomers by the usual free radical techniques. The resultant polymers have recurrent pendant side-chains terminated with an oxazoline or oxazine ring. Such rings give the polymers unique and valuable properties. Thus, such polymers are typically solid, fusible and soluble resins which can be molded or applied as coatings and then, by treatment with polycarboxylic acids, cured into hard, tough, infusible, adherent, cohesive and solvent-resistant articles, coatings, etc.

DETAILED DESCRIPTION OF THE INVENTION

The reaction between the bis-oxazoline or -oxazine and acrylic acid is conveniently conducted at a moderate temperature such as about 60°–100° C. and in the presence of a conventional polymerization inhibitor. While not essential, a reaction medium which is an inert solvent for the reactants and products facilitates the process. Suitable solvents include acetonitrile, dimethylformamide, chlorobenzene and perchloroethylene. When the reaction is essentially complete, the solvent is removed under vacuum, leaving the monomeric compound (I) in substantially quantitative yield. These products are typically viscous, light yellow liquids, soluble in many organic solvents.

The above products can be polymerized alone or with other polymerizable vinyl monomers by known techniques. Suitable comonomers include the acrylic acids and their esters, amides and nitriles, styrene, vinyl chloride, vinyl esters, olefins, such as ethylene, propylene, butadiene, isoprene, etc., maleic and itaconic acids, esters and anhydrides, and the like. The known free-radical-generating catalysts are useful, for instance the organic peroxides, azobis compounds, actinic light, electron beams or other high energy radiation.

The polymers produced as above described are typically thermoplastic solids that can be cast or molded. Being soluble in many organic solvents, they can also be used as surface coatings. In the latter utility the pendant oxazoline or oxazine rings contribute strong adhesion on most surfaces, as well as corrosion inhibition on metallic surfaces. Also, such groups enable the cross-linking of the polymer by reaction with a polycarboxy compound. The latter may be a monomeric polycarboxylic acid or it may be a polymeric material bearing a multiplicity of carboxyl groups. Such polymers include the polymers and copolymers of acrylic acid, maleic acid, itaconic acid and the like.

The bis-oxazolines and -oxazines used as starting materials for the present invention constitute a well known family of which many species are known and others can be made by methods similar to those used to make the known members. Representative members of the family are disclosed in U.S. Pat. Nos. 3,563,920, 3,763,177 and 3,758,629 all of which are hereby incorporated herein by reference. In general, such compounds correspond to the formula above, wherein the two oxazoline or oxazine rings (or one of each) are linked together by a chemical bond or an inert linking group, such linkages being in the 2-position on each ring. Suitable linking groups include alkylene groups of 1 to 10 or more carbon atoms, oxa-alkylene (sometimes called oxyalkylene or alkyleneoxy) groups or the corresponding thia-alkylene groups, alkenylene groups, arylene groups and the like.

The acrylic acid reactant may be acrylic acid itself, methacrylic acid, α-chloroacrylic acid, α-cyanoacrylic acid, α-butylacrylic acid or other α-substituted acrylic acid wherein the substituent does not inhibit the polymerizability of the acid or its esters.

SPECIFIC EMBODIMENTS OF THE INVENTION

The following examples illustrate the practice of the invention.

Example 1

Acrylic Acid +2,2'-Oxydiethylene-bis-(2-oxazoline)

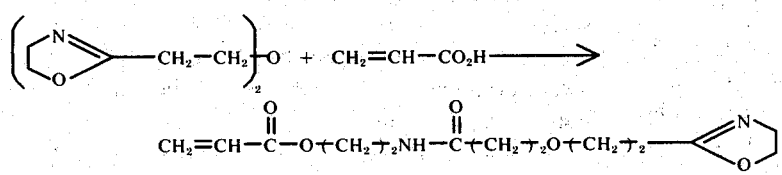

Equimolar amounts of glacial acrylic acid (0.80 g, 0.011 moles) and the oxazoline (2.33 g, 0.011 moles) were dissolved in approximately 7 ml. of dry acetonitrile containing 0.001 g of tert-butyl catechol as a polymerization inhibitor. This reaction mixture was heated for 2 hours at 84° C. Removal of solvent on a rotating evaporator (70°–75° C/0.1 mm) gave essentially a theoretical amount of a viscous yellow liquid. This product was very soluble in acetonitrile and soluble to some extent in methyl methacrylate, methylene chloride or acetone. Infrared and nmr analysis supported the proposed oxazoline structure.

Homopolymerization

To a 3 g sample of this oxazoline-substituted acrylate was added 1% by weight of azobis-isobutytonitrile (AIBN). Upon heating in an oven at 60° C for 8 hours, a light yellow transparent, somewhat rubbery polymer was obtained.

EXAMPLE 2

Acrylic Acid + 2,2'-Tetramethylene-bis-(2-oxazoline)

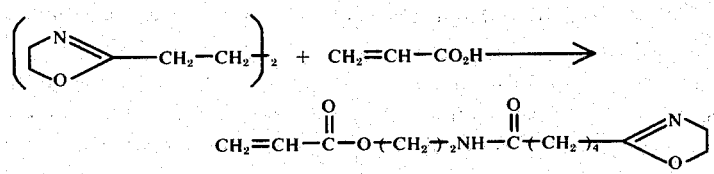

Equimolar amounts of glacial acrylic acid (0.67 g, 0.009 moles) and the oxazoline (1.8 g, 0.009 moles) were dissolved in 5 ml. of dry acetonitrile containing 0.001 g of tert-butyl catechol. The reaction mixture was heated for 2 hours at 84° C followed by removal of solvent on a rotating evaporator (50°–70° /0.1 mm). Essentially a theoretical weight of product was obtained as a very viscous, yellow liquid. Infrared and nmr analysis supported the above structure.

Homopolymerization

Bulk polymerization of this monomer with 1% by weight of AIBN at 60° C for 8 hours gave a cream-colored, opaque, tough, rubbery polymer.

Example 3

Acrylic Acid + 2,2'-Octamethylene-bis-(2-oxazoline)

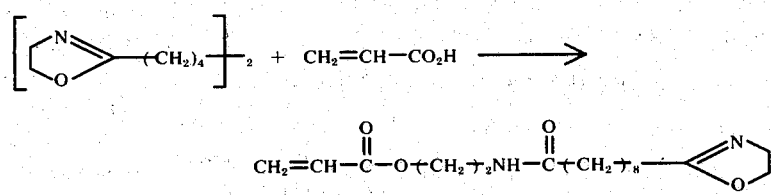

Heating approximately equimolar amounts of glacial acrylic acid (0.48 g, 0.0067 moles) and the oxazoline (1.5 g, 0.0059 moles) in 4.3 ml of dry acetonitrile containing tert-butyl catechol as an inhibitor gave 1.97 g of a yellow, viscous liquid. Nmr and IR analysis corroborated the structure. The monomeric product was partially soluble in acetone, methylene chloride and methyl methacrylate.

Homopolymerization

Bulk polymerization with 1% by weight AIBN at 60° C for 8 hours gave a light yellow rubbery solid.

Example 4

Acrylic Acid + 2,2'-Thiodiethylene-bis-2-oxazoline

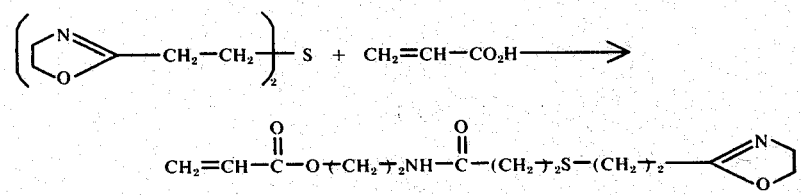

Equimolar quantities of 2,2'-thiodiethylene-bis-2-oxazoline (1.97 g., 8.63 mmoles) and acrylic acid (0.63 g., 8.63 mmoles) in 5.6 ml of dry acetonitrile containing (0.001 g) of tert-butyl catechol were heated at 84° C for 2 hours. Removal of solvent gave essentially a theoretical yield of a yellow, viscous liquid which was identified as the amido-ester substituted oxazoline shown above.

Homopolymerization

Bulk polymerization of a sample of the above product with 1% by weight of AIBN (60° C for 8 hrs.) gave a yellow colored, rubbery homopolymer.

Example 5

Methacrylic Acid + 2,2'-Oxydiethylene-bis-(2-oxazoline)

Equimolar quantities of glacial methacrylic acid (0.8 g, 0.009 moles) and the bis-oxazoline (1.8 g, 0.009 moles) in 5.1 ml of dry acetonitrile containing tert-butyl catechol were heated at 84° C for 2 hrs. Removal of solvent gave a theoretical recovery of the light, yellow viscous amido-ester substituted oxazoline shown above.

Homopolymerization

Bulk polymerization with 1% by weight AIBN (60% C/8 hrs) produced a yellow resinous solid.

Example 7

Methacrylic Acid + (2,2'-Octamethylene-bis-(2-oxazoline)

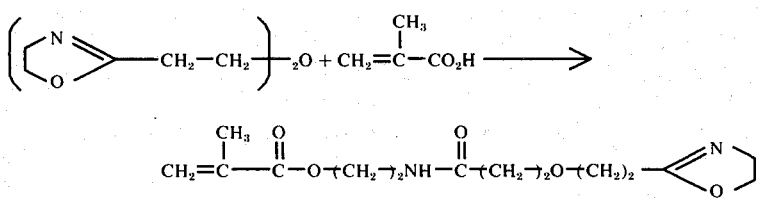

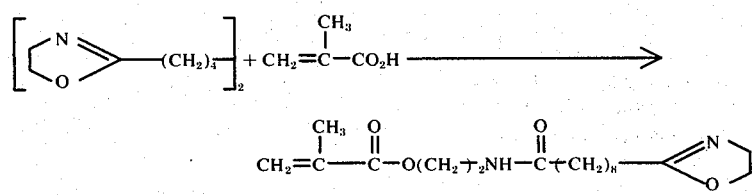

Equimolar amounts of glacial methacrylic acid (0.82 g, 0.009 moles) and the oxazoline (2.00 g, 0.009 moles) in 5.7 ml of dry acetonitrile (containing tert-butyl catechol inhibitor) were heated at 85° C for 2 hrs. Removal of solvent under vacuum gave a theoretical yield of the light yellow, liquid monomer.

Homopolymerization

Bulk polymerization of the above monomer with 1% by weight of AIBN at 60° C for 8 hrs gave a very tough, light yellow polymer suitable for coating or binder applications.

Example 6

Methacrylic Acid + 2,2'-Tetramethylene-bis-(2-oxazoline)

Equimolar amounts (5.9 moles) of glacial methacrylic acid and the bis-oxazoline was combined in 4.3 ml of dry acetonitrile and heated for 2 hr at 84° C. After removal of solvent a light, viscous, liquid residue was obtained. This material was identified as the amido-ester-oxazoline substituted methacrylate according to infrared and nmr analysis.

Homopolymerization

Bulk polymerization of the above methactylate with 1% by weight AIBN at 60° C/8 hrs gave a very tough, honey-colored resin.

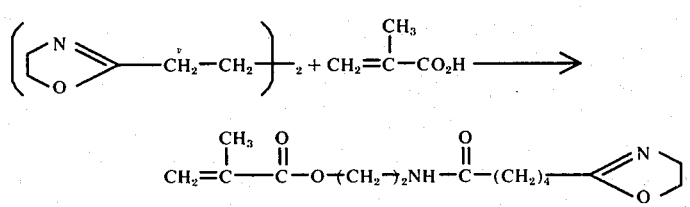

Example 8

Methacrylic Acid + 2,2'-Thiodiethylene-bis-(2-oxazoline)

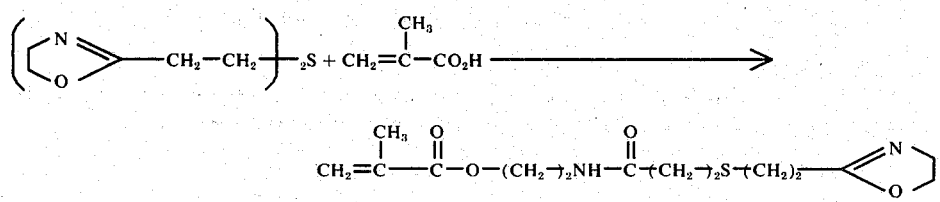

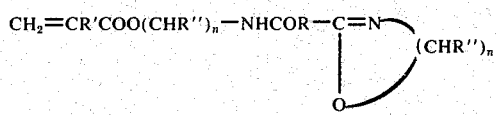

Equimolar amounts of glacial methacrylic acid (0.88 g, 10.07 mmoles) and bis-oxazoline (2.30 g, 10.07 mmoles) in 6.5 ml of dry acetonitrile (containing t-butyl catechol) were heated for 2 hrs. at 84° C. Removal of solvent gave 3.02 g (95% yield) of a yellow, viscous liquid which was identified as the amido-ester-oxazoline substituted methacrylate shown above.

Homopolymerization

Bulk polymerization of the above methacrylate with 1% by wt. of AIBN at 60° C/8 hr gave a tough, amber-colored resin.

While the above-described polymers, as well as copolymers of the above monomers with other polymerizable vinyl monomers, are useful per se for making cast or molded objects and can be used for protective coatings by application from a suitable solvent, they are especially useful for such purposes when mixed with curing agents having a multiplicity of carboxyl groups. Such curing agents include not only simple polycarboxylic acids but also polymers and copolymers of acrylic or methacrylic acid, maleic acid or anhydride, itaconic acid or anhydride, or the like. For this purpose, only a very small proportion, such as 1%, of the cross-linker produces a very significant cure when the mixture is subjected to a mild heat treatment such as 100° C. for 5 minutes, though larger amounts, up to about 20% by wt. or more, can be used. Such cure results in increasing the hardness, toughness, tensile strength, water resistance, solvent resistance, and heat resistance of the resin.

I claim:

1. A compound having the formula $$CH_2=CR'COO(CHR'')_n-NHCOR-C=N\underset{O}{\overset{}{\diagdown}}(CHR'')_n$$

wherein
R is alkylene of up to 10 carbon atoms, $CH_2CH_2OCH_2CH_2-$ or $-CH_2CH_2SCH_2CH_2-$,
R' is hydrogen or $CH_3$,
R'' is hydrogen and
n is the integer 2.

2. The compound of claim 1 where in R is $-(CH_2)_4-$, $-(CH_2)_8-$, $-CH_2CH_2OCH_2CH_2-$ or $-CH_2CH_2SCH_2CH_2-$.

* * * * *